United States Patent [19]

Rentél et al.

[11] Patent Number: 4,719,304

[45] Date of Patent: Jan. 12, 1988

[54] PROCESS FOR PREPARING 2-AMINOBENZOTHIAZOLES

[75] Inventors: Heinz Rentél, Kronberg im Taunus; Theodor Papenfuhs, Frankfurt am Main, both of Fed. Rep. of Germany

[73] Assignee: Hoechst Aktiengesellschaft, Frankfurt am Main, Fed. Rep. of Germany

[21] Appl. No.: 878,191

[22] Filed: Jun. 25, 1986

[30] Foreign Application Priority Data

Jun. 27, 1985 [DE] Fed. Rep. of Germany ....... 3522941

[51] Int. Cl.⁴ .......................................... C07D 277/82
[52] U.S. Cl. ................................................. 548/164
[58] Field of Search ................................. 548/161, 164

[56] References Cited

U.S. PATENT DOCUMENTS

| | | | |
|---|---|---|---|
| 4,113,732 | 9/1978 | Opgenorth et al. | 548/164 |
| 4,363,913 | 12/1982 | Clark et al. | 548/164 |
| 4,563,533 | 1/1986 | Rentél et al. | 548/164 |

OTHER PUBLICATIONS

Nippon Kayaku, Derwent and Japio abstracts of Japanese Patent Application 57-9774, published Jan. 19, 1982.
G. Hawley, Condensed Chemical Dictionary, Tenth Edition, p. 920 (1981), QDSC32.
E. Rideal, Concepts in Catalysis, Chapter 2, p. 5 (1968), Academic Press, NY.

*Primary Examiner*—Mary E. Ceperley

[57] ABSTRACT

Process for preparing 2-aminobenzothiazoles of the formula (1)

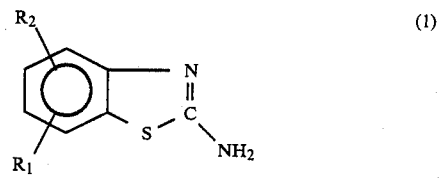

in which $R_1$ and $R_2$ denote hydrogen or halogen atoms or alkyl$_{C_1-C_4}$, alkoxy$_{C_1-C_4}$ or nitro groups, by reacting phenylthioureas of the formula (2)

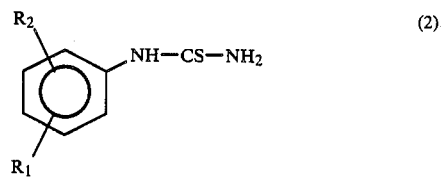

in which $R_1$ and $R_2$ have the abovementioned meanings, at temperatures of 20° C. to 130° C. in 70–100% strength sulfuric acid in the presence of catalytic amounts of bromine, hydrogen bromide, sodium bromide, potassium bromide or ammonium bromide which comprises carrying out the reaction in the presence of a finely divided solid which has a large specific surface area and is inert under the reaction conditions.

3 Claims, No Drawings

PROCESS FOR PREPARING 2-AMINOBENZOTHIAZOLES

It is known to prepare 2-aminobenzothiazoles by cyclizing appropriate phenylthioureas in 85–100% strength sulfuric acid in the presence of catalytic amounts of bromine, hydrogen bromide, sodium bromide, potassium bromide or ammonium bromide at temperatures of 20°–130° C. (Japanese Patent Application Sho 57-9774; U.S. Pat. No. 4,363,913). However, the reaction does not proceed uniformly, so that side reactions (sulfonation, bromination, hydrolysis of the phenylthiourea with, in some instances, subsequent substitutions of the type first mentioned) give rise to qualitatively unsatisfactory product mixtures which require expensive purification and (in the case of small solubility differences between the target products and by-products) give poor yields.

It has now been found, surprisingly, that 2-aminobenzothiazoles of the general formula (I)

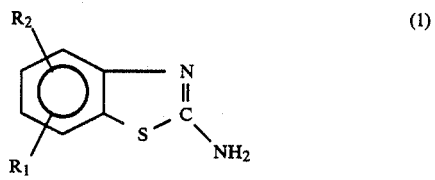

in which $R_1$ and $R_2$ denote hydrogen or halogen atoms, such as fluorine, chlorine, bromine or iodine atoms, or alkyl$_{C_1-C_4}$, alkoxy$_{C_1-C_4}$ or nitro groups, can be obtained in high yields and in high purity while avoiding side reactions by reacting phenylthioureas of the general formula (2)

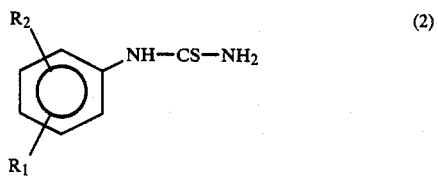

in which $R_1$ and $R_2$ have the abovementioned meanings, in a manner known per se (see above) if finely divided solids of high specific surface area which are inert under the reaction conditions are additionally present.

Suitable solids of the type mentioned include for example amorphous silicas (kieselguhr), which are commercially available as, for example, ®Celite, ®Dicalite, ®Clarcel, ®VDK fillerguhr, ®Fina/Optima filter aids, highly active bleaching earths, for example prepared from the clay mineral montmorrillonite (commercially available as ®Terrana, ®Tonsil or ®Clarit), vulcanic liparite or quartz porphyric glasses ("Perlite"), precipitated silicas (commercially available for example as ®Ultrasil, ®Silcasil, ®Vulcasil, ®Silcatron or ®Sipernat), silica gels (for example as commercial products ®Syloid, ®Gasil, ®Lucilite, ®Silicon, ®Diamantgel) or pyrogenic silicas (on the market for example as ®Aerosil, ®Cab-O-Sil, ®HDK) and activated carbons (for example as commercial products ®Actibon, ®Carboraffin, ®Norit, ®Acticarbone, ®Alcarbon, ®Brilonit, ®Darco, ®Eponit).

The process according to the invention is carried out in detail by dissolving the phenylthiourea of the said formula (2) in 1–10 times the amount by weight of sulfuric acid of a concentration of 70 to 100% with stirring, then adding the finely divided solid according to the invention in an amount of 0.1 to 0.01 percent by weight, based on the starting phenylthiourea of the formula (2), and, after adding the catalyst in the form of bromine, hydrogen bromide, sodium bromide, potassium bromide or ammonium bromide, performing the cyclization at temperatures of 20° to 130° C., preferably at 40° C.–90° C.

The resulting offgas ($SO_2$) is converted in an alkali metal hydroxide solution gas wash to reusable bisulfite solution.

The progress of the cyclization reaction is easily monitored by analytical methods, for example thin layer, gas or liquid chromatography.

When all the starting material has been reached, the cyclization mixture is diluted with water, undissolved portions are removed by clarifying filtration, and the resulting 2-aminobenzothiazole of the said formula (1) is separated out in the form of its sulfate by cooling, or is precipitated as a free base by adding sufficient amounts of an alkali metal hydroxide or of aqueous ammonia solution and isolated by filtration.

The examples below will illustrate the process according to the invention in more detail without limiting it thereto.

EXAMPLE 1

An enameled vessel is charged with 150 kg of concentrated sulfuric acid. While stirring, 49.3 kg of 4-nitrophenylthiourea are added at room temperature, the mixture is stirred, and 2 kg of Perlite are then added. 2 kg of ammonium bromide are then added in portions, and the reaction is completed at 100° C.–105° C. in 2.5–3 hours. When 4-nitrophenylthiourea is no longer detectable, the reaction mixture is discharged under pressure onto 750 kg of water and clarified at about 95° C. To the clarified filtrate are added with cooling 160 kg of 25% strength ammonia solution until a pH value of 3.5 has been reached, and the precipitated 2-amino-6-nitrobenzothiazole is filtered off at about 70° C. and washed with hot water until neutral.

Drying leaves 44.9 kg of 2-amino-6-nitrobenzothiazole (melting point 247° C.), which corresponds to a yield of 91.0% of theory. The product gives a clear solution in 80% strength phosphoric acid. HPLC (high performance liquid chromatography) analysis shows no trace of impurity.

EXAMPLE 2

49.3 kg of 4-nitrophenylthiourea are dissolved with stirring in 150 kg of concentrated sulfuric acid, and 2.5 kg of finely ground kieselguhr are added. 2.5 kg of bromine are then added in the course of an hour, during which the temperature reaches 45° C.–50° C. The temperature is then raised to 95° C.–100° C. and is maintained there for about 2–3 hours until 4-nitrophenylthiourea is no longer detectable. The reaction mixture is then discharged onto 800 kg of water, which is followed by clarifying at about 95° C. and adjustment of the pH value to 3.5 with aqueous sodium hydroxide solution. The precipitated 2-amino-6-nitrobenzothiazole is filtered off hot and is washed with hot water until neutral.

Drying leaves a 2-amino-6-nitrobenzothiazole having a melting point of 247° C., which gives a clear solution in 80% strength phosphoric acid at 50° C. HPLC analysis shows no trace of a contamination. The amount isolated is 44.6 kg, which corresponds to a yield of 90.4% of theory.

EXAMPLES 3-10

Example 1 is repeated, except that the 4-nitrophenyl-thiourea and the solid according to the invention are replaced by the materials mentioned in the table below:

| Example No. | Thiourea (compound of the formula (2)) | Solid according to the invention | End product | Yield/purity (HPLC) |
|---|---|---|---|---|
| 3 | 46.6 kg of 2-chlorophenyl-thiourea | 2.5 kg of celite | 2-amino-4-chloro-benzothiazole | 92% of theory/ 99% pure |
| 4 | 50 kg of 2-methyl-4-chloro-phenylthiourea | 3 kg of tonsil | 2-amino-4-methyl-6-chlorobenzo-thiazole | 91.5% of theory/ 99.1% pure |
| 5 | 45.5 kg of 4-methoxyphenyl-thiourea | 4.5 kg of perlite | 2-amino-6-methoxybenzo-thiazole | 90.5% of theory/ 98.6% pure |
| 6 | 55.3 kg of 3,4-dichlorophenyl-thiourea | 3.5 kg of celite | 2-amino-5(7),6-dichlorobenzo-thiazole (mixed isomers) | 96.1% of theory/ 99.4% pure |
| 7 | 55.3 kg of 3,4-dichlorophenyl-thiourea | 2.0 kg of activated carbon | 2-amino-5(7),6-dichlorobenzo-thiazole (mixed isomers) | 95.8% of theory/ 98.9% pure |
| 8 | 46.6 kg of 4-chlorophenyl-thiourea | 2.0 kg of kieselguhr | 2-amino-6-chloro-benzothiazole | 94.8% of theory/ 99.2% pure |
| 9 | 55.3 kg of 2,4-dichlorophenyl-thiourea | 3.0 kg of Clarcel | 2-amino-4,6-dichlorobenzo-thiazole | 95.0% of theory/ 99.4% pure |
| 10 | 55.3 kg of 2,4-dichlorophenyl-thiourea | 3.0 kg of Perlite | 2-amino-4,6-dichlorobenzo-thiazole | 96.1% of theory/ 99.2% pure |

COMPARATIVE EXAMPLE

Example 1 is repeated, except that no solid according to the invention (Perlite) is added, affording a 6-nitro-2-aminobenzothiazole having a melting point of 238° C.-240° C., which does not give a clear solution in 80% strength phosphoric acid at 60° C. and contains the following impurities (HPLC, measured against authentic comparative substances):
1.6% of 4-nitroaniline
1.8% of 2-bromo-4-nitroaniline 2,6-dibromo-4-nitroaniline
0.6% of 4-nitrophenylthiourea.

We claim:

1. A process for preparing 2-aminobenzothiazoles of the formula (1)

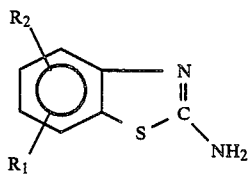

(1)

in which $R_1$ and $R_2$ denote hydrogen or halogen atoms or alkyl$_{C_1-C_4}$, alkoxy$_{C_1-C_4}$ or nitro groups, by reacting phenylthioureas of the formula (2)

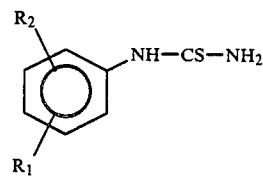

(2)

in which $R_1$ and $R_2$ have the above-mentioned meanings, at temperatures of 20° C. to 130° C. in a reaction medium comprising the phenylthiourea of formula (2) and 70-100% strength sulfuric acid, the reactions being catalyzed by a bromine-containing catalyst, which comprises adding to the reaction mixture 0.1 to 0.01 percent by weight, based on the starting phenylthiourea of formula (2), of amorphous, pyrogenic or precipitated silica; silica gel; kieselguhr; bleaching earth; vulcanic liparite or quartz porphyric glasses or activated carbon as a finely divided solid having a large specific area and being inert under the reaction conditions, and subsequently adding a catalytic amount of the bromine-containing catalyst, which consists essentially of bromine, hydrogen bromide, sodium bromide, potassium bromide or ammonium bromide.

2. The process as claimed in claim 1, wherein the reaction is carried out at 40° C. to 90° C.

3. The process as claimed in claim 1, wherein the 2-aminobenzothiazole product of formula (1) is obtained in a purity of at least about 98%, as determined by high performance liquid chromatography.

* * * * *